US010451539B2

(12) United States Patent
Saha et al.

(10) Patent No.: US 10,451,539 B2
(45) Date of Patent: Oct. 22, 2019

(54) MICROSCALE SENSORS FOR DIRECT METROLOGY OF ADDITIVELY MANUFACTURED FEATURES

(71) Applicants: Sourabh Saha, Livermore, CA (US); Robert Matthew Panas, Dublin, CA (US); Michael A. Cullinan, Austin, TX (US); Ian Seth Ladner, Livermore, CA (US)

(72) Inventors: Sourabh Saha, Livermore, CA (US); Robert Matthew Panas, Dublin, CA (US); Michael A. Cullinan, Austin, TX (US); Ian Seth Ladner, Livermore, CA (US)

(73) Assignees: Lawrence Livermore National Security, LLC, Livermore, CA (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/910,604

(22) Filed: Mar. 2, 2018

(65) Prior Publication Data
US 2019/0271635 A1   Sep. 5, 2019

(51) Int. Cl.
| | |
|---|---|
| *G01N 19/08* | (2006.01) |
| *B33Y 40/00* | (2015.01) |
| *G01B 7/16* | (2006.01) |

(52) U.S. Cl.
CPC ............ *G01N 19/08* (2013.01); *B33Y 40/00* (2014.12); *G01B 7/22* (2013.01)

(58) Field of Classification Search
CPC . G01N 3/08; G01N 19/08; G01B 7/22; G01L 5/00; G01L 5/16; G01L 9/0055; B33Y 40/00; G01R 27/08
(Continued)

(56) References Cited

U.S. PATENT DOCUMENTS

| | | | | |
|---|---|---|---|---|
| 7,265,476 B1 * | 9/2007 | Abushagur | ............ | H02N 1/004 |
| | | | | 310/309 |
| 7,548,011 B2 * | 6/2009 | Borovic | ................ | H02N 1/008 |
| | | | | 310/309 |

(Continued)

OTHER PUBLICATIONS

Espinosa, H. D., Y. Zhu and N. Moldovan. "Design and operation of a MEMS-based material testing system for nanomechanical characterization." Journal of Microelectromechanical Systems, vol. 16, No. 5, Oct. 2007, pp. 1219-1231.
(Continued)

*Primary Examiner* — Octavia Hollington
(74) *Attorney, Agent, or Firm* — Harness, Dickey & Pierce, PLC

(57) ABSTRACT

This invention relates to a microelectromechanical device for mechanical characterization of a specimen. In one embodiment the device may incorporate a substrate, at least one first flexure bearing and at least one second flexure bearing, both being supported on the substrate. First and second movable shuttles may be used which are supported above the substrate by the flexure bearings so that each is free to move linearly relative to the substrate. Ends of the movable shuttles are separated by a gap. A thermal actuator may be connected to one end of the first movable shuttle, and operates to cause the first movable shuttle to move in a direction parallel to the surface of the substrate in response to a signal applied to the thermal actuator. A first capacitive sensor may be formed between the first movable shuttle and the substrate, and a second capacitive sensor formed between the second movable shuttle and the substrate.

22 Claims, 9 Drawing Sheets

(58) Field of Classification Search
USPC .......................................................... 73/775
See application file for complete search history.

(56) References Cited

U.S. PATENT DOCUMENTS

| | | | | |
|---|---|---|---|---|
| 7,616,013 | B2* | 11/2009 | Messenger | G01D 5/18 |
| | | | | 324/415 |
| 7,980,133 | B2* | 7/2011 | Geen | G01C 19/5719 |
| | | | | 73/504.04 |
| 9,279,753 | B2* | 3/2016 | Espinosa | G01N 3/08 |
| 9,390,061 | B1* | 7/2016 | Deeds | G01R 27/2605 |

OTHER PUBLICATIONS

Bauer, J., Schroer, A., Schwaiger, R., Tesari, I., Lange, C., Valdevit, L., and Kraft, O., 2015, "Push-to-pull tensile testing of ultra-strong nanoscale ceramic-polymer composites made by additive manufacturing," Extreme Mechanics Letters, 8 pp.

Zhang, S.-J., Li, Y., Wang, Y.-K., Liu, L.-P., Wang, H.-D., Xiao, Y.-F., Yang, H., and Gong, Q., 2015, "Controlling Young's modulus of polymerized structures fabricated by direct laser writing," Applied Physics A, 118(2), pp. 437-441.

Cicha, K., Koch, T., Torgersen, J., Li, Z., Liska, R., and Stampfl, J., 2012, "Young's modulus measurement of two-photon polymerized micro-cantilevers by using nanoindentation equipment," Journal of Applied Physics, 112(9), p. 094906.

Haque, M., H. Espinosa and H. Lee (2010). "MEMS for in situ testing-handling, actuation, loading, and displacement measurements." MRS bulletin 35 May 2010, pp. 375-381.

Jayne, R. K., T. J. Stark, J. B. Reeves, D. J. Bishop and A. E. White "Dynamic Actuation of Soft 3D Micromechanical Structures Using Micro-Electromechanical Systems (MEMS)." Advanced Materials Technologies: 3.3 (2018): 1700293.

Niels, T., S. Tonny, J. Henri, L. Rob and E. Miko (1996). "Stiction in surface micromachining." Journal of Micromechanics and Microengineering 6(4): p. 385.

Zhu Y., A. Corigliano and H. D. Espinosa (2006). "A thermal actuator for nanoscale in situ microscopy testing: design and characterization." Journal of micromechanics and microengineering 16(2): p. 242.

Zhu, Y. and H. D. Espinosa (2005). "An electromechanical material testing system for in situ electron microscopy and applications." Proceedings of the National Academy of Sciences of the United States of America 102(41): pp. 14503-14508.

Hosseinian, E. and O. N. Pierron (2013). "Quantitative in situ TEM tensile fatigue testing on nanocrystalline metallic ultrathin films." Nanoscale 5(24, 2013, pp. 12532-12541.

Y. Zhu, N. Moldovan, and H. D. Espinosa, "A microelectromechanical load sensor for in situ electron and x-ray microscopy tensile testing of nanostructures," Appl. Phys. Lett., vol. 86, No. 1, 2005, 4 pp.

\* cited by examiner

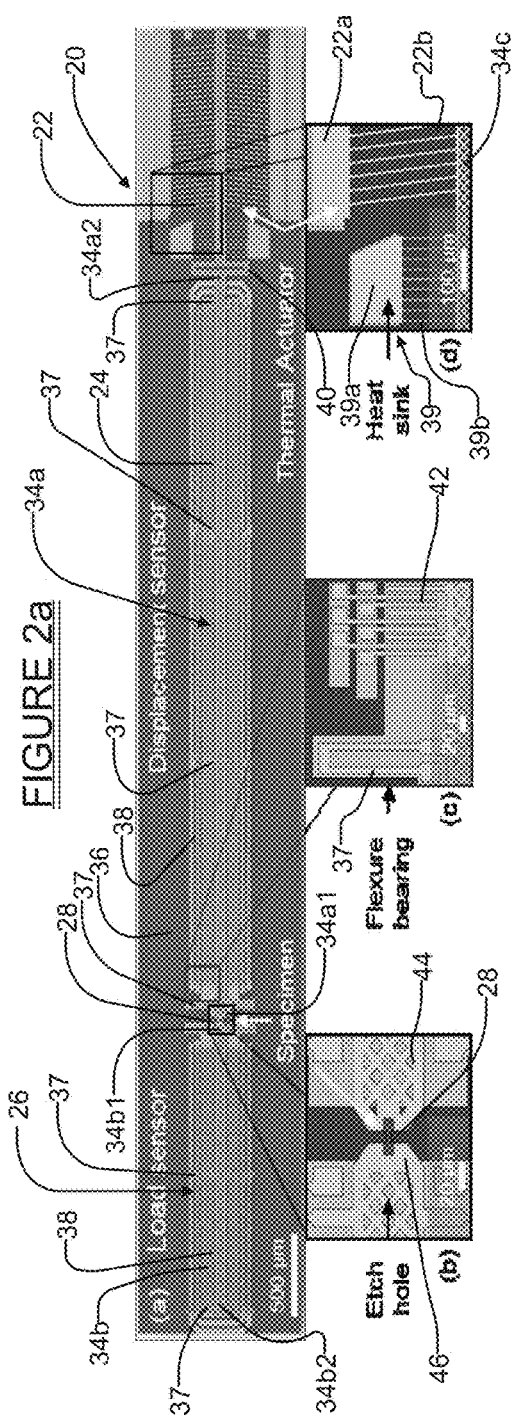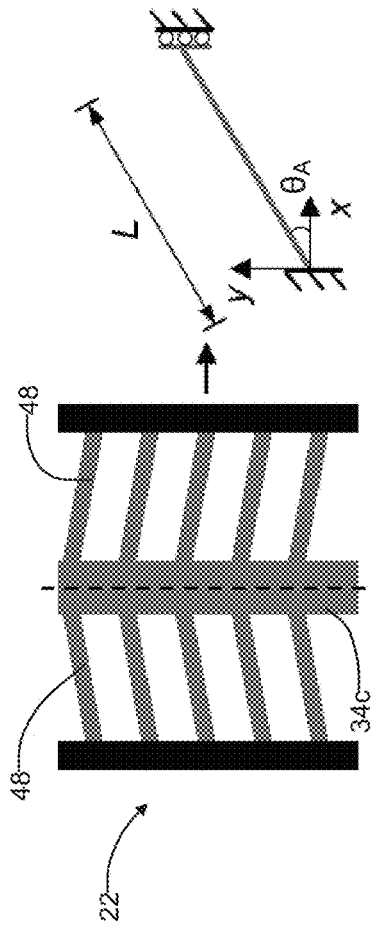

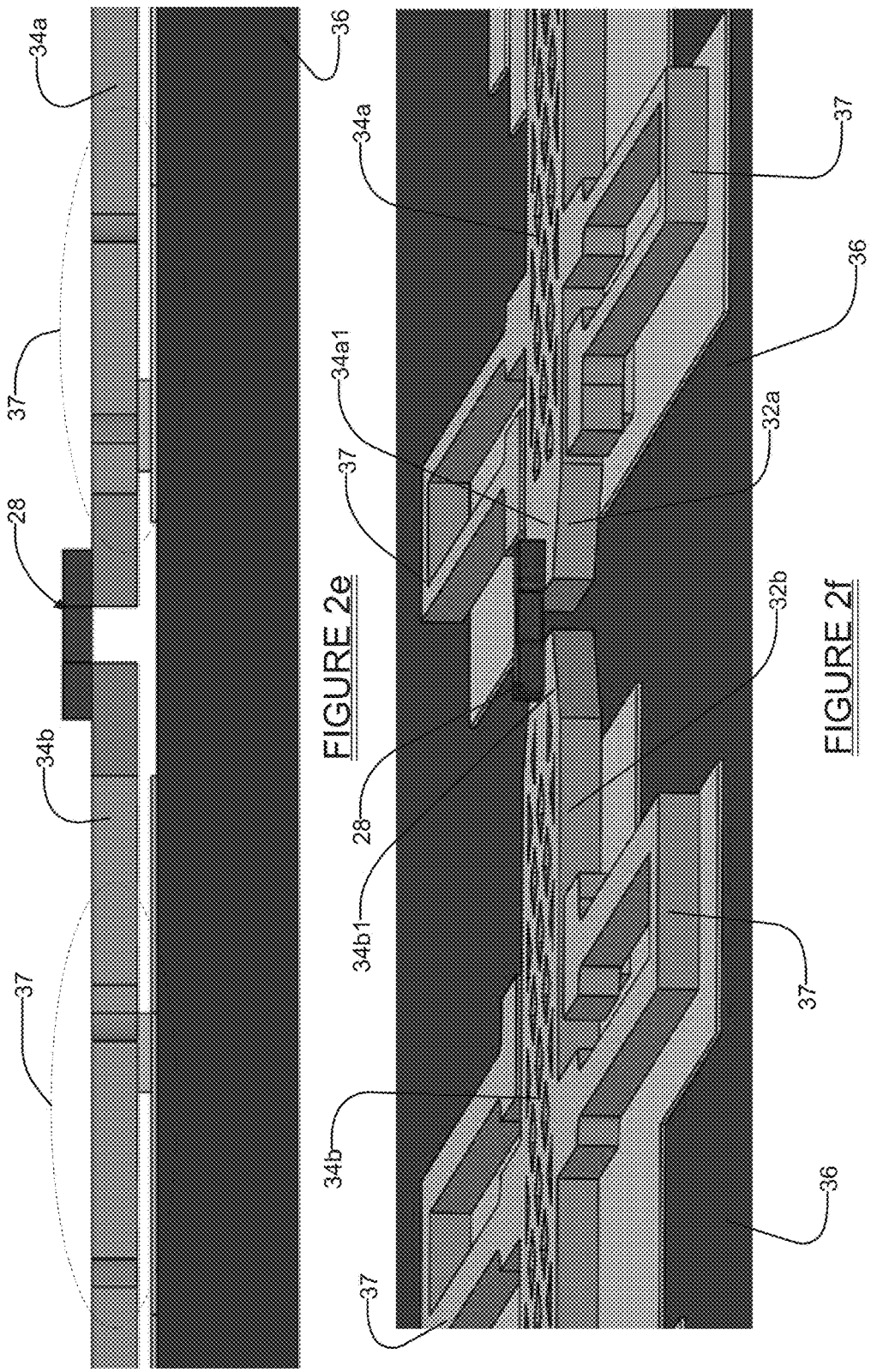

MICROSCALE SENSORS FOR DIRECT METROLOGY OF ADDITIVELY MANUFACTURED FEATURES

STATEMENT OF GOVERNMENT RIGHTS

The United States Government has rights in this invention pursuant to Contract No. DE-AC52-07NA27344 between the U.S. Department of Energy and Lawrence Livermore National Security, LLC, for the operation of Lawrence Livermore National Laboratory.

FIELD

The present disclosure relates to systems and methods for performing metrology of polymeric additively manufactured structures comprising submicron features, and more particularly to systems and methods for directly measuring the stress-strain response of additively manufactured part or structure with a force and displacement resolution that is relevant to quantifying the stress-strain response of the individual submicron features comprising the additively manufactured part.

BACKGROUND

This section provides background information related to the present disclosure which is not necessarily prior art.

Two-photon lithography is a popular technique to additively manufacture ("AM") complex 3D structures with submicron building blocks ("voxels"). This technique uses a nonlinear photo-absorption process to polymerize submicron features within the interior of the photopolymer resist material. After illumination of the desired structures inside the photoresist volume and subsequent development, the polymerized material remains in the prescribed three-dimensional form.

The availability of well-characterized resists for this process is determined by the ability to measure the mechanical properties of the printed structures. However, this characterization for newly developed custom resists is often hindered by the lack of process knowledge required to successfully fabricate a mechanically stable macroscale part. This deadlock between "print-before-measure" and "measure-before-print" can be resolved via direct metrology on the length scale of the elementary submicron voxel lines. Unfortunately, commercial techniques for such direct measurements on the 100 nm feature scale are not available today.

The specific problem of direct measurement of the mechanical properties of submicron printed features has not been solved in the past. Instead, indirect measurements have been performed by relying on the structural deformation response of assembled printed parts under loading. For example, Bauer et al., "Push-to-pull Tensile Testing of Ultra-strong Nanoscale Ceramic-polymer Composites Made by Additive Manufacturing," Extreme Mechanics Letters, 2015, have demonstrated indirect measurement of voxel-level properties via a load transfer framework. In addition, Zhang et al., "*Controlling Young's Modulus of Polymerized Structures Fabricated by Direct Laser Writing*," Applied Physics A, 118(2), pp. 437-441, 2015, and Cicha et al., "*Young's Modulus Measurement of Two-photon Polymerized Micro-cantilevers by Using Nanoindentation Equipment*," Journal of Applied Physics, 112(9), p. 094906, 2012, have demonstrated estimation of average bulk Young's modulus of elasticity by measuring the deformation of assembled structures. All of these techniques presuppose the ability to fabricate a mechanically stable, assembled structure. This is not guaranteed for a newly synthesized custom resist. In addition, all of these techniques generate structure-specific data that cannot be readily generalized beyond the specific structures tested. This is because these techniques comingle the material response (determined by fundamental material properties) and the structural response (determined by structural form), thereby making it infeasible to reliably separate the two effects.

The general problem of direct measurement of the mechanical properties of submicron features has been successfully solved in the past. For example, U.S. Pat. No. 9,279,753 B2 to Espinoza et al. (2016) for "*Microelectromechanical device and system*", discloses a microelectromechanical system ("MEMS") sensor for direct tensile testing of submicron features. In these sensors, the feature of interest is manually transferred to the sensing regions via pick-and-place techniques. The primary limitations of these devices for measurement of printed features are that (a) these sensors cannot be used to incorporate the printed features directly onto the sensors, and (b) pick-and-place techniques cannot be implemented to transfer the printed features onto the sensors. Direct printing of the features onto these sensors is not feasible because of the additional process compatibility requirements imposed by the AM process. Specifically, the liquid-phase development process after the AM step renders the sensors inoperative due to stiction, i.e., due to the effect of moving parts of the sensor collapsing onto each other under the influence of capillary forces generated during development. In addition, pick-and-place techniques for transfer of separately printed features is not practical due to the lower stiffness and strength of printed polymer parts as compared to that of the materials of interest for these prior art sensors (carbon nanotubes, silicon, metals). Thus, existing MEMS sensors for tensile testing are not appropriate for sensing of printed polymer parts.

Accordingly, it would be highly desirable to provide a system capable of directly measuring the mechanical properties of submicron features on a scale that is relevant to additively manufacture larger structures.

SUMMARY

This section provides a general summary of the disclosure, and is not a comprehensive disclosure of its full scope or all of its features.

In one aspect the present disclosure relates to a microelectromechanical device for mechanical characterization of a specimen. The device may incorporate a substrate, at least one first flexure bearing and at least one second flexure bearing, both being supported on the substrate. First and second movable shuttles may be used which are supported above the substrate by the flexure bearings so that each is free to move linearly relative to the substrate. Ends of the movable shuttles may be separated by a gap. A thermal actuator may be connected to one end of the first movable shuttle. The thermal actuator may operate to cause the first movable shuttle to move in a direction parallel to the surface of the substrate in response to a signal applied to the thermal actuator. A first capacitive sensor may be formed between the first movable shuttle and the substrate, and a second capacitive sensor may be formed between the second movable shuttle and the substrate.

In another aspect the present disclosure relates to a method for mechanical characterization of a specimen material using a microelectromechanical system (MEMS) device. The method may comprise applying specimen material across a gap formed between ends of a first movable shuttle and a second movable shuttle, such that the specimen material is rigidly affixed to the ends of the first and second movable shuttles. The method may further comprise axially moving the first movable shuttle to stretch or compress the specimen material in controlled fashion. The method may further comprise measuring a displacement of each one of the first and second movable shuttles.

In still another aspect the present disclosure relates to a method for forming a device able to perform mechanical characterization of submicron features of a specimen material. The method may comprise supporting a first movable shuttle above a substrate using a thermal actuator and at least one first flexure bearing, and supporting a second movable shuttle above the substrate using at least one second flexure bearing. The method may further comprise arranging distal ends of the first and second movable shuttles adjacent one another to enable the specimen material to be applied to, and to bridge, the distal ends. The method may further comprise arranging a thermal actuator in contact with the first movable shuttle to cause linear movement of the first movable shuttle when a signal is applied to the thermal actuator, and thus to apply at least one of a tensile stress and a compressive stress to the sample. The method may further comprise arranging a capacitive sensing subsystem adjacent the first and second shuttles such that a displacement of both of the first and second movable shuttles is detectable for subsequent analysis. This enables a specimen material to be applied across a gap formed between ends of the first movable shuttle and the second movable shuttle, such that the specimen material is able to be rigidly affixed to the ends of the first and second movable shuttles.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2a is an enlarged view of the system of FIG. 1a;

FIG. 2b is an enlarged plan view of a portion of the system of FIG. 2a illustrating the facing distal ends of the two movable shuttles with a voxel of additively printed material formed thereon and bridging the distal ends of the two movable shuttles;

FIG. 2c is an enlarged plan view of a portion of one of the system of FIG. 2a showing one of the flexure bearings used to support one of the movable shuttles for linear movement;

FIG. 2d is an enlarged plan view of a portion of the system of FIG. 2a illustrating a portion of the thermal actuator and a portion of the heat sink of the system;

FIG. 2e is a highly enlarged side view of the portion of the system shown in FIG. 2b;

FIG. 2f is a highly enlarged perspective view of the portion of the system shown in FIG. 2b;

FIG. 3 is a plan view of just a portion of the thermal actuator of the system showing the chevron style pairs of beams that connect the thermal actuator to the first movable shuttle, along with a diagram to help explain the forces that the thermal actuator applies;

FIG. 4 is a highly enlarged schematic representation of a portion of the differential capacitive sensor used by the system of FIG. 2a;

FIG. 5 is a lumped mechanical model of the electrothermal actuator of the system of FIG. 2a;

Corresponding reference numerals indicate corresponding parts throughout the several views of the drawings.

DETAILED DESCRIPTION

Figure 1A:
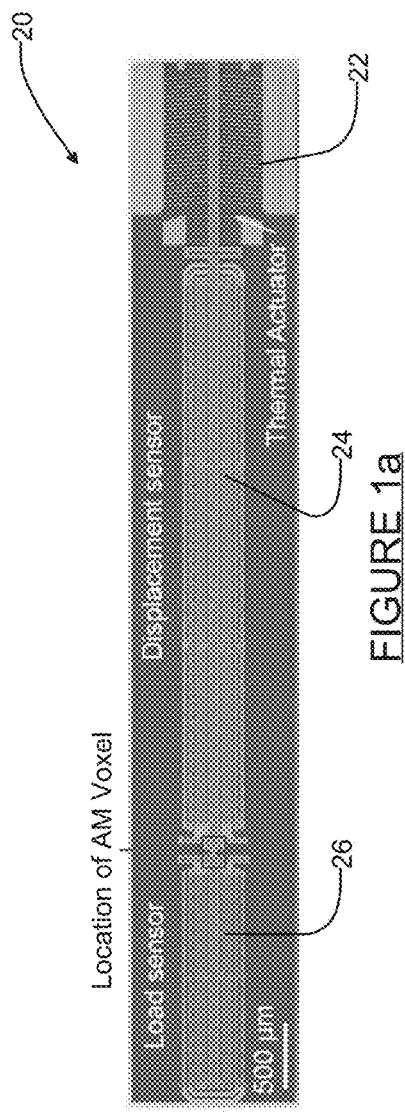
FIG. 1a is a plan view of a first embodiment of a system in accordance with the present disclosure for measuring mechanical properties of a voxel of additively manufactured specimen material deposited directly onto the system.

Example embodiments will now be described more fully with reference to the accompanying drawings.

The system and method of the present disclosure enables direct measurement of the mechanical properties of submicron features on a scale that is relevant to additively manufacture larger structures. Specifically, the present disclosure enables measuring (a) stress-strain response of the elementary features, (b) strength of the elementary features and (c) strength and stiffness of a single stitch interface, i.e., the interface between two elementary features or between two assembled structures. The present disclosure overcomes the limitations of prior art systems and methods by enabling the printing of polymer features directly on top of the MEMS (Microelectromechanical System) sensors. To enable this integration, our devices have been designed to include features that suppress the stiction effect. This integration enables directly measuring the force-displacement response of the elementary features on the submicron length scale without comingling it with any other structural response. Such high-fidelity material property data has never been reported for additively manufactured materials at the submicron scale. At the present time, there are believed to be no other pre-existing devices or systems are able to integrate a MEMS sensor with additively manufactured parts. It will also be noted that simply combining existing tensile testing MEMS sensors with AM features is not a practical solution because prior art type MEMS sensors would be rendered inoperative by such attempts. The MEMS sensors must therefore be redesigned to overcome this inoperability.

Initially it will be understood that graphene, polymers and other nanomaterials are emerging candidate materials for transistors, MEMS, and microfluidic devices. However, one of the critical factors limiting their widespread use is limited knowledge of scale dependent material properties, such as elastic modulus and elongation at break, which emerge in the submicron region, Gao et al., "*Materials Become Insensitive to Flaws at Nanoscale: Lessons From Nature*", Proc. Natl. Acad. Sci., Vol. 100, No. 10, pp. 5597-5600 (2003). A key challenge in characterizing submicron scale features is handling of the sample during the integration between the tested part and metrology system. To address this challenge, previous studies have focused on solving a subset of this problem by adopting in-situ metrology techniques. For example, previous studies have presented in-situ mechanical characterization of multi-walled carbon nanotubes (see, e.g., Espinoza et al., "*Design and Operation of a MEMS-based Material Testing System for in-situ Electron Microscopy Testing of Nanostructures*", J. Microelectromech. S. Vol. 16, No. 5, p. 12341 (2007)), and MEMS sensors to characterize strain tunability of graphene resonators (see, e.g., G. Sun et al., *A Method to Manufacture Repeatable Graphene-based MEMS devices at Wafer-Scale*," Proc. ASME 2016 Int. Manuf. Sci. Eng. Conf., pp. MSEC 2016-8567 (2016)). The present disclosure extends this concept of in-situ metrology and presents embodiments of MEMS tensile testers that can generate force-displacement responses for a variety of nanomaterials including those additively manufactured.

Figure 1B:
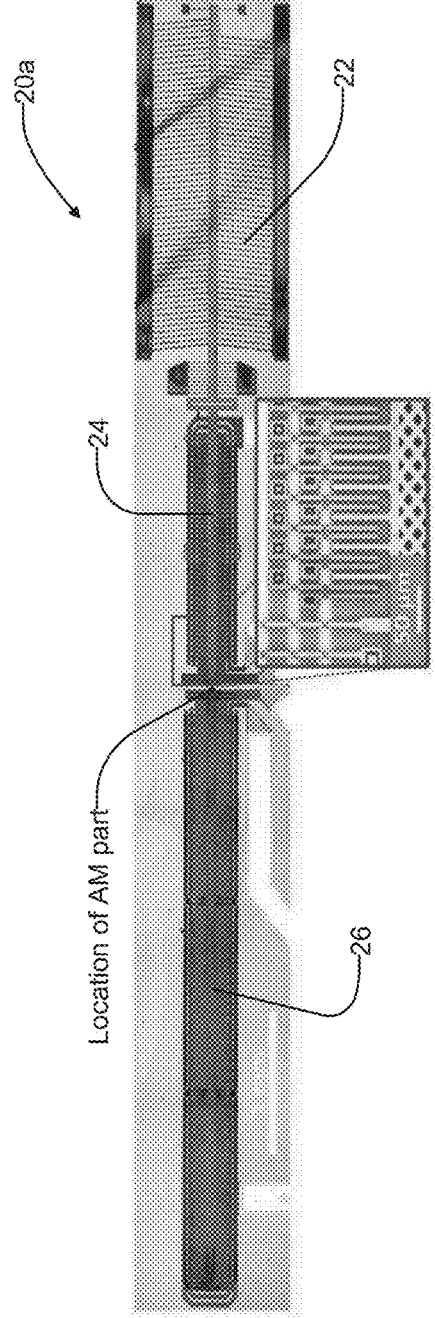
FIG. 1b is a plan view of a second embodiment of a system in accordance with the present disclosure for measuring mechanical properties of a three dimensional additively manufactured part formed directly on the system.

Referring to FIG. 1a, a micromechanical system (MEMS) tensile tester device 20 in accordance with one embodiment of the present disclosure is shown which is suitable for use with testing of voxel (volumetric pixel) of additively manufactured material specimens. The device 20 is optimized for testing a single line or trace of an additively manufactured (AM) material specimen which may be formed directly on the device 20. FIG. 1b illustrates a tensile tester device 20a which is similar in construction to the device 20 but which is optimized for testing a completed three dimensional part (i.e., a part formed of a large number of lines or traces of material). The devices 20 and 20a both include an electromechanical thermal actuator ("ETA") 22, a displacement sensor 24 and a load (i.e., force) sensor 26. With the device 20, the length of the displacement sensor 24 is significantly greater than the length of the load sensor 26, but with the device 20a the length of the load sensor 26 is greater than the length of the displacement sensor 24. The sensor lengths vary between the two embodiments to account for the difference in range and resolution of force and displacements to be measured during testing of a single line (sensor 20) or multiple lines (sensor 20a). The relationship between range/resolution and sensor size is provided later in this disclosure. The sensors 20 and 20a demonstrate the feasibility of integrating an AM voxel or complete AM 3D part onto a MEMS type sensing component. The AM voxel or complete 3D AM part may be fabricated on the device 20 or 20a, for example, by using the commercial Nanoscribe GT system via two-photon lithography (see S. K. Saha et al., "Effect of Proximity of Features on the Damage Threshold During Submicron Additive Manufacturing Via Two-Photon Polymerization," in Journal of Micro and Nano-Manufacturing 5.3 (2017): 031002." The devices 20 and 20a form MEMS type sensors that specifically address (i) the force and displacement resolution and range requirements for AM parts and (ii) resolve fabrication challenges. Specifically, the devices 20 and 20a include stiction control features to resolve fabrication errors and allow wet transfer of specimen parts.

Referring to FIG. 2a, the device 20 will be described in greater detail. As noted above, devices 20 and 20a are essentially identical except for the dimensions of the various subsections thereof. In FIG. 2a the ETA 22 is in the form of a chevron style ETA which pulls on a specimen material 28 that is itself attached to the displacement stage formed by the displacement sensor 24 portion. The ETA 22 may incorporate integrated beams 22b coupled at one end thereof to a central stage 34c and at the opposite ends to a pad 22a which receives an input signal from an external device (not shown). Double parallelogram folded-beam pairs 37 shown in FIG. 2c suspend and guide the first movable shuttle 34a of the displacement stage formed by the displacement sensor 24. The first movable shuttle has a first end 34a1 and a second end 34a2. A second movable shuttle 34b is aligned along a common longitudinal axis with the first movable shuttle 34a and includes a first end 34b1 and a second end 34b2. The first ends 34a1 and 34b1 are both free and the material specimen is applied (e.g., printed or formed) to bridge the free ends 34a1 and 34b1. The free ends 34a1 and 34b1 are adjacent to each other with a finite gap between the two. Gaps in the range of 1 micrometer to 250 micrometer are desirable for testing of AM specimens. The second end 34a2 of the first movable shuttle 34a is operatively coupled to the central stage 34c of the ETA 22, while the second free end 34b2 of the second movable shuttle 34b is secured through flexure bearings to a substrate 36 above which the movable shuttles 34a and 34b are supported. The substrate may be formed from any suitable material, but in one preferred form may be a layer of silicon nitride on top of a silicon wafer.

The specimen material 28 specimen may comprise a wide variety of materials. For example, and without limitation, the specimen material 28 may comprise an additively manufactured part, a plurality of biological cells, a soft material (e.g., polymeric nanowires, Deoxyribonucleic acid (DNA) threads), or 2D materials (e.g., graphene nanosheets). The movable shuttles 34a and 34b are supported above the substrate 36 and constrained to move only linearly by a plurality of linearly spaced apart flexure bearings 37. Flexure bearings form a class of commonly used high-precision bearings that rely on flexing (i.e., bending) of members to constraint motions along the undesired directions. Double parallelogram flexure bearings have been used here to generate a set of linear bearings that constraint motion in all directions except translations along the longitudinal axis of the movable shuttles. In this example four linearly spaced apart flexure bearings 37 are used to support the first movable shuttle 34a while three flexure bearings 37 are used to support the second movable shuttle 34b. However, it will be appreciated that these numbers may be changed to suit a specific application. For example, the device 20a, because of the different lengths of the load sensor 26 and the displacement sensor 24, may require a greater number of flexure bearings 37 to be used with the load sensor than with the displacement sensor.

FIGS. 2a, 2d 2i and 2j also illustrate a heat sink subsystem 39 having a heat sink pad 39a and a plurality of heat sink beams 39b. The heat sink beams 39b are coupled to the central stage 34c of the ETA and also to the heat sink pad 39a that is coupled to the substrate. The heat sink subsystem 39 is located close to the connection between the central stage of the ETA and the second end of the first movable shuttle to prevent leakage of heat from the ETA into the first movable shuttle. A thermal resistor 40 is introduced at the junction between the first movable shuttle and the ETA to ensure that heat transfer from the ETA to the substrate through the heat sink pad is preferred over heat transfer from the ETA into the first movable shuttle. Each of the displacement sensor 24 (displacement stage) and the load sensor 26

Figure 2G:
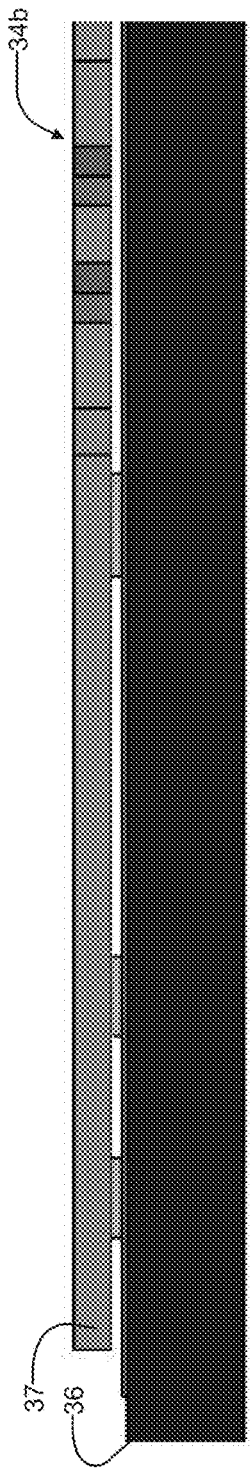
FIG. 2g is a highly enlarged side view of the portion of the system shown in FIG. 2c.
Figure 2H:
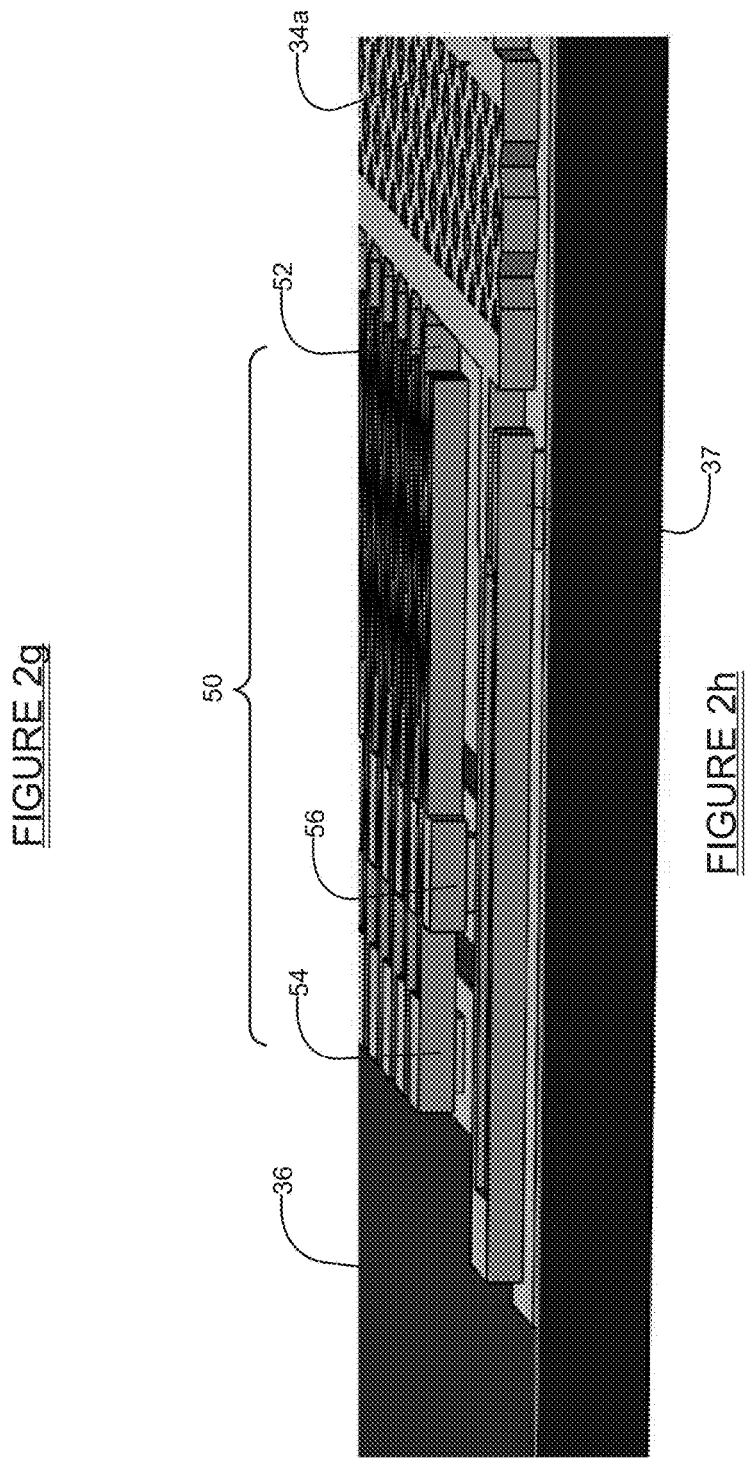
FIG. 2h is a highly enlarged perspective view of the portion of the system shown in FIG. 2c.
Figure 2I:
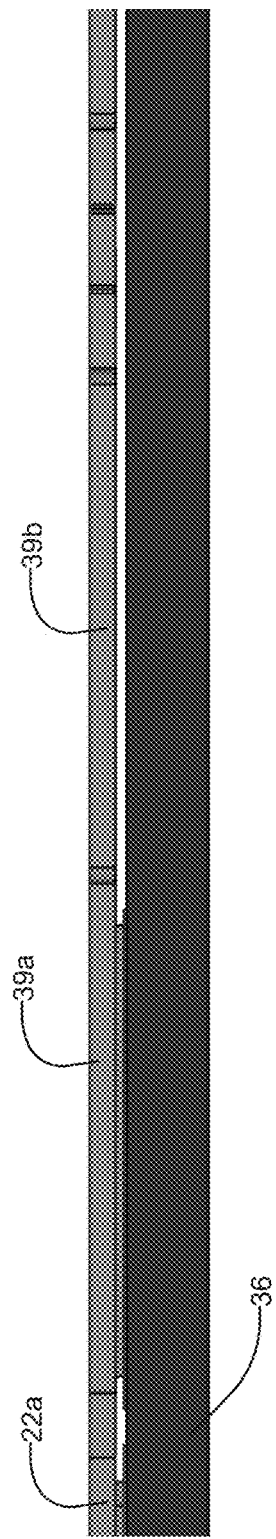
FIG. 2i is a highly enlarged side view of the portion of the system shown in FIG. 2d.
Figure 2J:
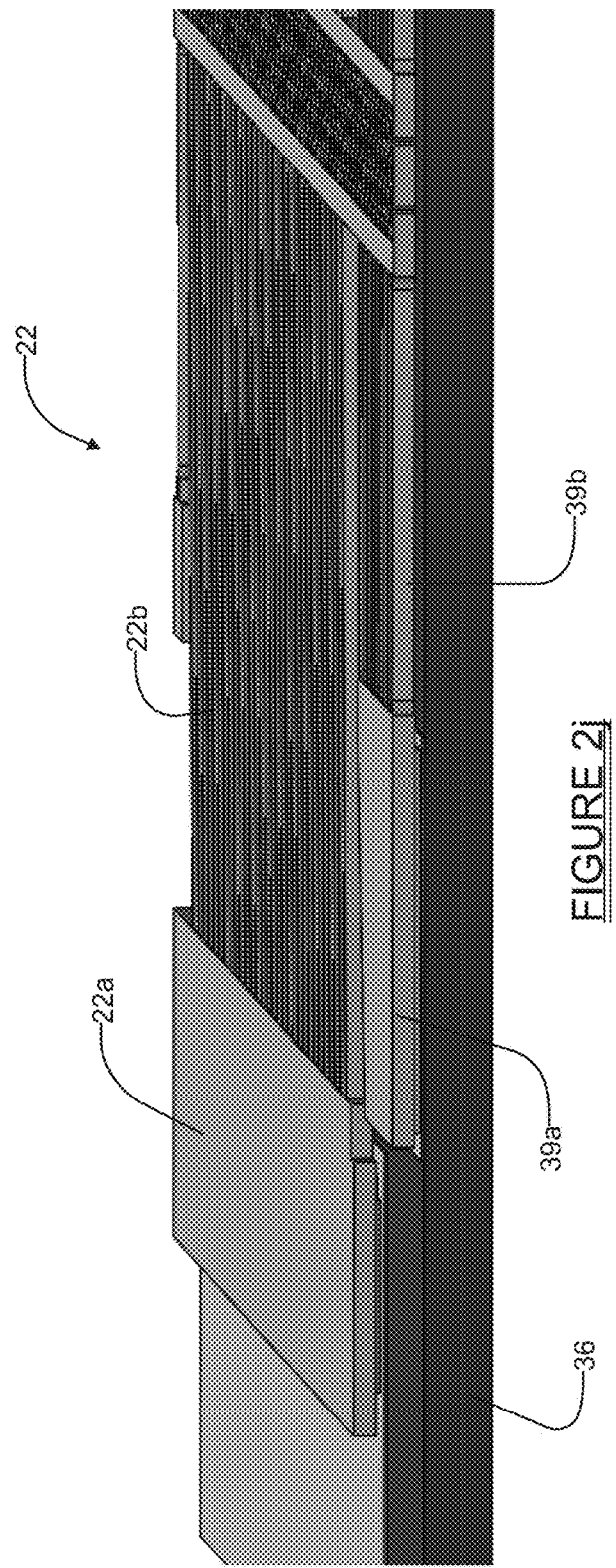
FIG. 2j is a highly enlarged perspective view of the portion of the system shown in FIG. 2d.
Figure 4:
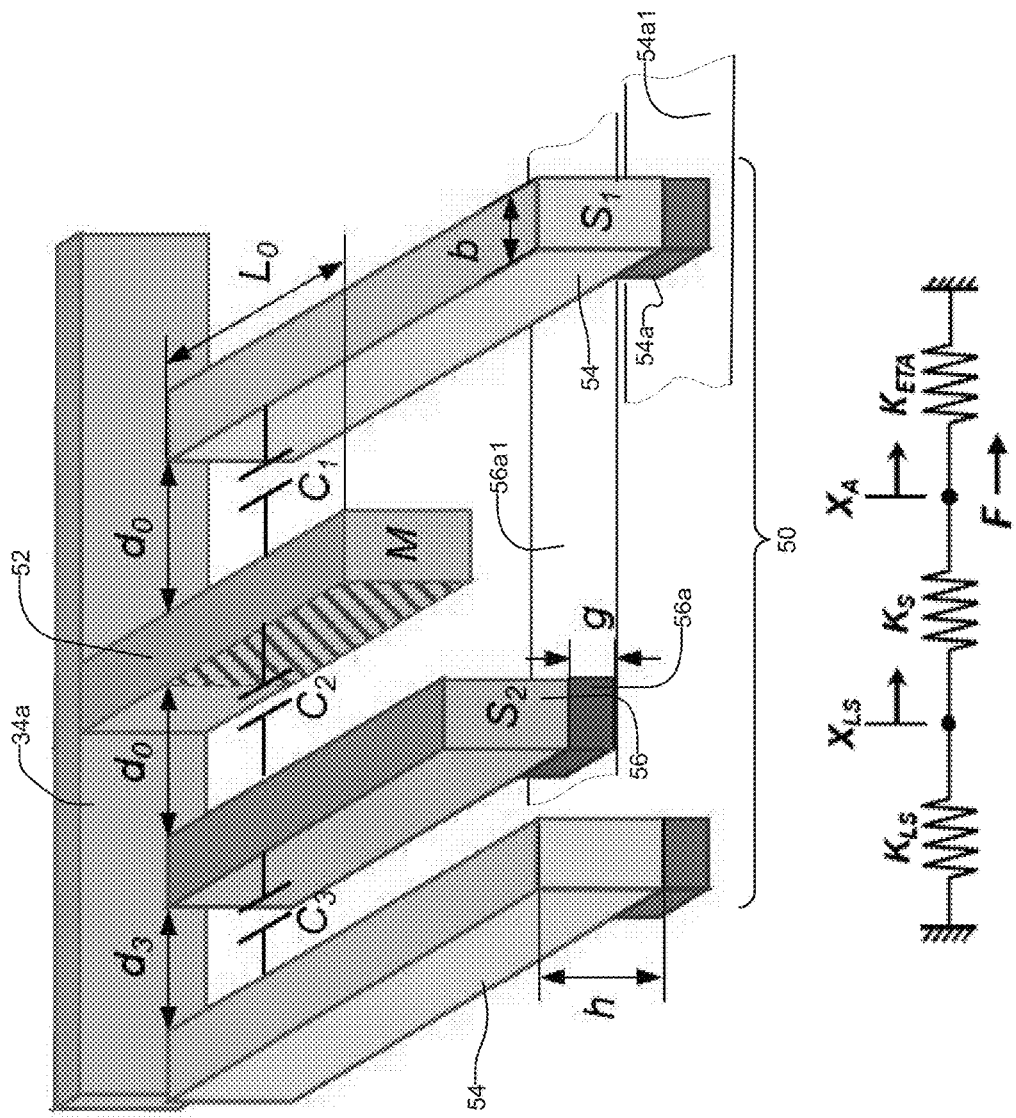

(load stage) may incorporate a differential capacitor sensor subsystem 38. Each differential capacitor subsystem 38 may be formed using set of fingers 42 as indicated in FIG. 2c and supported on the substrate 36 via folded beam flexures 37 as shown in FIGS. 2g and 2h. Each capacitor subsystem 38 comprises individual capacitive units 50 in the form of a set of movable and fixed fingers. In this embodiment each set of four fingers comprises one movable finger (52) and 3 stationary fingers (54 and 56) fixed to the substrate 36 as shown in FIG. 4. Free ends of both the displacement sensor 24 and the load sensor 26 form specimen platforms 44 and 46, as shown in FIG. 2b, onto which portions of the specimen 28 may be deposited or formed through an AM process.

With further reference to FIG. 3, the chevron style ETA 22 may comprise a symmetrical arrangement of the beams 22b, which form inclined beams. The beams 22b are coupled to and extend from the central stage 34c to the fixed support pad 22a along opposite sides of the central stage in a fixed-guided boundary condition. This enables the beams 22b of the ETA 22 to generate an axial force on the first movable shuttle 34a upon Joule heating of the beams 22b, which causes longitudinal movement of the first movable shuttle, and in turn results in movement of the specimen 28 (placing the specimen under either tension or compression), and movement of the second moveable shuttle 34b. This actuation method is displacement controlled and applies a known strain to the specimen 28. Force generated F by the ETA 22 can be evaluated using Equation 1 below:

$$F = 2N_{ETA} E A_{ETA} \alpha \Delta T \sin \theta_A \qquad \text{Equation 1}$$

Here "$N_{ETA}$" is the number of beam sets 22b (i.e., number of beam pairs in the symmetric arrangement across the central stage 34c), "E" the elastic modulus, "$A_{ETA}$" the cross sectional area of each beam, "$\alpha$" the coefficient of thermal expansion, "$\Delta T$" the average beam 22b temperature, and "$\theta_A$" the incline beam angle of the beam 22b as shown in FIG. 3. Compression versus tension can be generated from the ETA by simply changing the sign of the incline angle $\theta_A$. Stiffness "seen" by the ETA 22, represented by the term "$K_{ETA}$", combines all of the components rigidly connected to the ETA: displacement sensor double parallelogram style flexure bearings 37 $K_{disp}$, heat sink beams 39b $K_{HS}$, and ETA beams 22b. The double parallelogram style flexure bearings 37 are used to reduce out-of-plane motion of the first and second movable shuttles 34a and 34b and to help ensure only linear movement of the first and second movable shuttles along a common longitudinal axis. The stiffnesses are defined by Equations 2, 3, and 4 below:

$$K_{disp} = 2N_{disp} \frac{E b_{disp}^3 h_{disp}}{L_{disp}^3} \qquad \text{Equation 2}$$

$$K_{HS} = 2N_{HS} \frac{E b_{HS}^3 h_{HS}}{L_{HS}^3} \qquad \text{Equation 3}$$

$$K_{ETA} = 2N_{ETA} \left( \sin^2\theta_A \frac{E b_{ETA}^3 h_{ETA}}{L_{ETA}} + \cos^2\theta_A \frac{E b_{ETA}^3 h_{ETA}}{L_{ETA}^3} \right) + K_{HS} + K_{disp} \qquad \text{Equation 4}$$

Here, "L" and "b" are the beam length and width respectively, "h" is the beam thickness which is preferably the same across all components to simplify fabrication. If these parameters are not same for all components, then the length, width and thickness of the appropriate component (identified by the subscripts ETA: ETA, HS: heat sink, and disp: flexure bearings of first movable shuttle) should be used in equations 2 to 4.

The differential capacitance sensor 38 shown in FIG. 2a may be comprised of individual capacitive units 50 as shown in highly enlarged fashion in FIG. 4. Each capacitive unit 50 may contain two sets of fingers wherein one set is stationary with respect to the substrate and the other set is movable and attached to the movable shuttles 34a or 34b. In one embodiment, each capacitive unit 50 unit may include one moving finger 52 (M) attached to a respective movable shuttle, that is, either a portion of movable shuttle 34a or a portion of movable shuttle 34b, but in this example movable shuttle 34a, as well as three stationary fingers 54 ($S_1$) and 56 ($S_2$). Each stationary finger 54 and 56 has a respective contact pad 54a and 56a, bonded to a separate conductive trace 54a1 and 56a1 on the substrate 36. This capacitive unit 50 is repeated in a periodic manner with adjacent units sharing the same stationary fingers 54 to form a capacitor sensor subsystem 38. Increasing the number of capacitive units 50 in the sensor subsystem 38 increases the resolution of the sensors. As the dynamic range of the sensor or specimen stiffness increases, the sensor's change in capacitance is lowered due to an inverse relationship with parallel plate spacing and a direct relationship with smaller resolution. The most effective way to recover the lost capacitance is to increase the number of capacitive unit cells due to the direct relationship, but the tradeoff is sensor size. Each trace, 54a1 and 56a1, connects all the stationary fingers, 54 ($S_1$) and 56 ($S_2$) respectively, of each unit cell in parallel to form the total individual capacitance values for the sensor subsystem 38. The contact pads 54a and 56a also help to provide a gap "g" between their respective finger (i.e., finger 54 or 56) and an upper surface of the substrate 36, thus essentially suspending the majority of the length of each finger 54 and 56 above the substrate 36. Initially, the gaps (i.e., spacings) between the moving finger 52 and the stationary fingers 54/56 are equal, "$d_0$". The individual capacitance values are shown in Equations 5 through 7 below:

$$C_1 = n\varepsilon \left( \frac{A_1}{d_0 + \Delta d} + \frac{A_2}{g} + 0.65 \frac{A_1}{h} \right) \qquad \text{Equation 5}$$

$$C_2 = n\varepsilon \left( \frac{A_1}{d_0 - \Delta d} + \frac{A_2}{g} + 0.65 \frac{A_1}{h} \right) \qquad \text{Equation 6}$$

$$C_3 = n\varepsilon \left( \frac{A_1}{d_3} + 0.65 \frac{A_1}{h} \right) \qquad \text{Equation 7}$$

where "n" is number of units, "$\varepsilon$" is relative permittivity of air, "$A_1$" is the initial overlap area shown in the blue cross hatch pattern in FIG. 4, "$\Delta d$" is the displacement of the moving finger 52 (M), $A_2$ is initial overlap of the finger 52 and a substrate below it, "g" is the gap between stationary fingers 54/56 and the substrate 36, and "$d_3$" is the spacing being finger 54 ($S_1$) and finger 56 ($S_2$). Displacement by $\Delta d$ generates a change in capacitance, $\Delta C$, which is defined by Equation 8 below:

$$\Delta C \approx \frac{2n\varepsilon A_1}{d_0^2} \Delta d \qquad \text{Equation 8}$$

where $\Delta C$ is set to 0.1 fF for the displacement resolutions of each sensor 20 and 20a (FIGS. 1a/2a and FIG. 1b). This value is twice the previously reported value of 0.05 fF by Espinosa, cited above, to account for additional noise generated from the wired connection between the MEMS device and a MS3110 capacitive readout IC on a separate printed circuit board (PCB).

Mechanical Model

A lumped mechanical model shown in FIG. 5 may be used to tune the geometry of the ETA 22, heat sinks, and displacement and load sensor flexure bearings 37. The resulting system of equations may be provided as follows:

$$x_s = x_A - x_{LS} \quad \text{Equation 9}$$

$$K_{LS} x_{LS} = K_s x_s \quad \text{Equation 10}$$

$$K_s x_s + K_{ETA} x_A = F \quad \text{Equation 11}$$

where "x" is the displacement and "K" is the stiffness of the load sensor 24, subscript LS is load sensor, and the specimen 28, "s", respectively. Approximate values for the device 20 and 20a specimen stiffness, "$K_s$", are 140 N/m and 8 N/m respectively. $K_{ETA}$ is set to be much greater than $K_s$ and $K_{LS}$ to maintain displacement control. The range of the load sensor 26 for each device 20 and 20a is defined by $K_{LS}$.

Stiction Control

Figure 6:
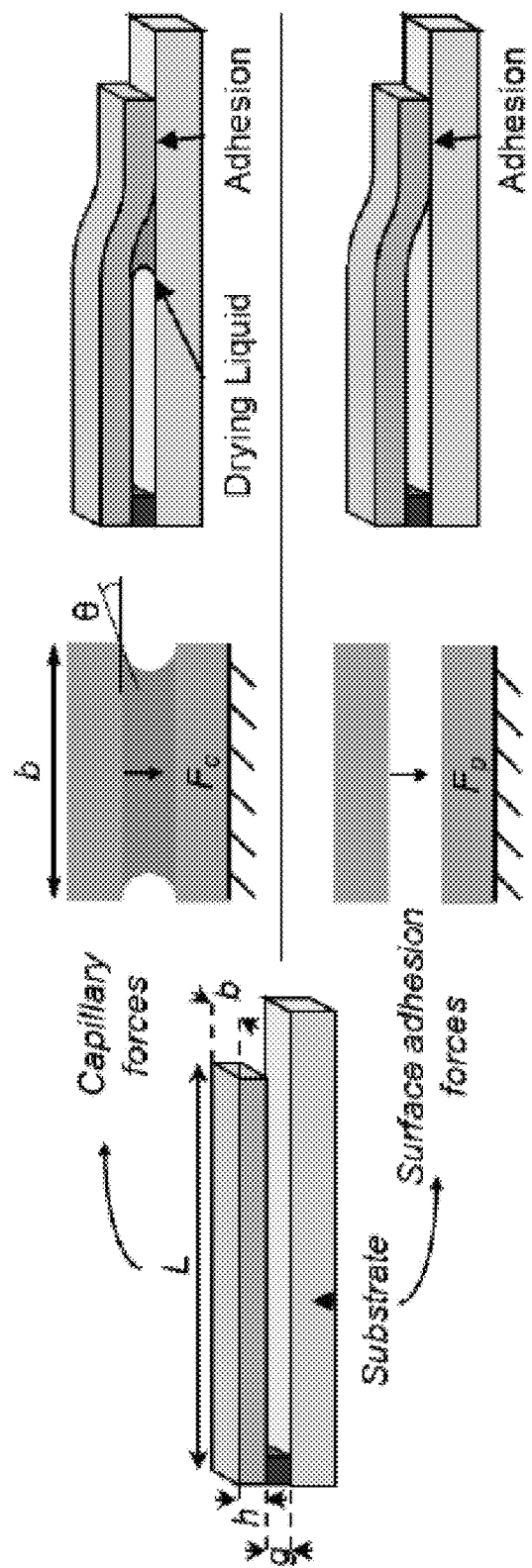
FIG. 6 is a series of simplified illustrations to help explain how stiction can occur when drying, after the wet release etch, and can produce capillary forces sufficiently large to permanently adhere the newly suspended structures to the substrate.

Stiction is a failure mode that is common in MEMS devices. Stiction occurs when drying, after the wet release etch, produces capillary forces sufficiently large to permanently adhere the newly suspended structures to the substrate. This is shown in FIG. 6. Traditionally MEMS devices will only encounter this failure mode during the release etch, however a robust stiction analysis would allow the tensile tester to utilize wet transfer methods for specimens such as additively manufactured parts, biological cells and other soft materials.

Capillary and surface-to-surface adhesion are the main sources of stiction this design will encounter during wet transfer. Mastrangelo and Hsu, "*A Simple Experimental Technique for the Measurement of the Work of Adhesion of Microstructures*," Technical Digest IEEE Solid-State Sensor and Actuator Workshop, pp. 208-212, 1992, introduced characteristic equations for both the elastocapillary and peel number respectively. The elastocapillary number, NEC, determines if the elastic energy in a suspended geometry is greater than the applied capillary forces. Peel number, NP, determines if the suspended geometry will release when brought in contact with another surface. Traditionally, the numbers are set to one and solved for the critical length (see Hsu, Id.), as indicated in Equations 12 and 13 below:

$$L_{EC} = \left[ \frac{2Eg^2 h^3}{9\gamma_l \cos\theta \left(1 + \frac{h}{b}\right)} \right]^{0.25} \quad \text{Equation 12}$$

$$L_P = \left( \frac{3Eg^2 h^3}{8\gamma_s SF} \right)^{0.25} \quad \text{Equation 13}$$

where $\gamma_l$ represents liquid surface tension, $\theta$ represents liquid contact angle, and $\gamma_s$ represents solid surface tension.

Vertical and horizontal stiction analysis was conducted on all suspended elements in the design with safety factors of 1.5 for capacitor fingers 54/56 and a minimum of 2 for flexure bearings 37 and thermal actuator beams 22b. For the configuration described herein, in Equation 12 or 13 during horizontal analysis, g is either $d_0$ or $d_3$, and "h" and "b" are interchanged.

Figure 7A:
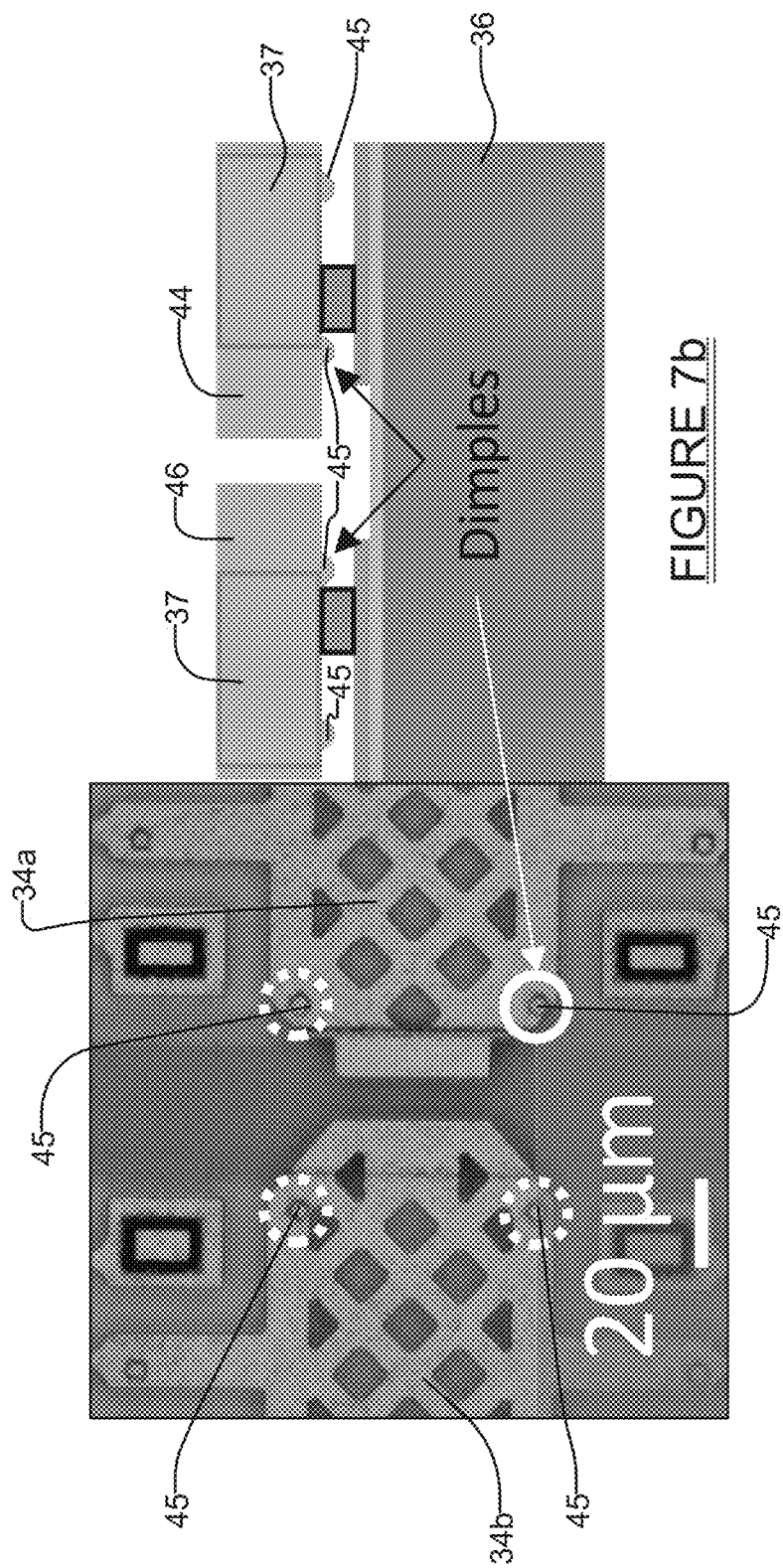
FIG. 7a is a top view of the platform region showing dimples for stiction control.
Figure 7B:
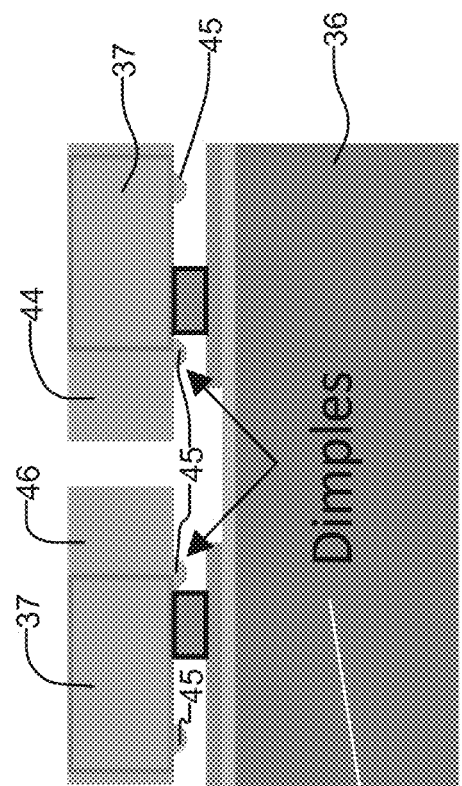
FIG. 7b is a cross-sectional view of the platform region showing dimples for stiction control.

In order to achieve the range for the displacement sensor 24 of device 20 and the load sensor 26 of device 20a, the overall length of the shuttle 34a/34b (i.e., length including both movable portions 34a and 34b) is preferably in the millimeter range, which necessitates additional methods to help reduce stiction. This may be accomplished by adding hemispherical dimples to the base to reduce the contact area (see, e.g., N. Tas et al. "*Striction in Surface Micromachining*," J. Micromechanics Microengineering, Vol. 6, No. 4, pp. 385-397 (1996)). Spacing between the dimples 45 may be set to about 60 μm in order to achieve a minimum safety factor of 2 and maximum of 6 of peel number and elastocapillary number. Dimples on the bottom surface of the movable shuttles 34a and 34b in the region close to the platforms 44 and 46 are shown in FIGS. 7a and 7b.

Device 20 and Device 20a Results

The device layer is 8 μm of heavily doped polysilicon with E=170 GPa and $\alpha = 2.5 \times 10^{-6}$. The performance of Design 1 and 2 is given in the Table 1 below with a $\Delta T = 550°$ C.

TABLE 1

| MEMS tensile tester designed performance. | | |
|---|---|---|
|  | Design 1 | Design 2 |
| $K_s$ | 140 N/m | 8 kN/m |
| Max F | 265 uN | 25.1 mN |
| F Resolution | 30 nN | 3 uN |
| Max Δd | 1.5 um | 3.1 um |
| Δd Resolution | 0.25 nm | 2 nm |

Electro-thermomechanical finite element analysis (FEA) of Design 2 demonstrates that the platform 44 temperature only increases to 31° C. which limits the impact of the ETA on the specimen temperature and thus validity of tensile testing data. Displacement at the tip is 4.13 μm, which is a good match for displacement without a specimen. Additionally, the out-of-plane displacement is less than 10 nm. This ensures high accuracy and precision during specimen loading.

The present disclosure presents two embodiments of MEMS tensile testers for the characterization of nanomaterials. These MEMS sensors provide high precision, in-situ metrology for determining mechanical properties of nanomaterials. In addition, elastocapillary and peel numbers are considered during the design of all suspended structures to allow wet transfer of nanomaterials post fabrication.

One method for fabricating the MEMS sensors is through the PolyMUMPs approach. A silicon nitride layer, Nitride 1, is deposited to act as a hydrofluoric acid resistant electrical insulator. The base polysilicon layer, Poly 1, is deposited and patterned as the electrical traces for 37, 54a1, and 56a1 between the device fingers and the electrodes. Two sacrificial oxide layers, Oxide 1 and 2, create the gap, g, in FIG. 4, and open the holes for connections 54a and 56a between Poly 1 and the device layer, Poly 2. A thick polysilicon layer, Poly 2, is deposited, but not patterned to improve pattern transfer for the metallization step. Another nitride layer, Nitride 2, is deposited and patterned to open connections between Poly 2 and the Au/Cr metal electrode stack forming the electrode. The metallization step uses a liftoff process to pattern the Au/Cr electrode stack, Gold 1. After liftoff, Poly 2 is patterned and etched using deep reactive ion etching (DRIE) to form all of the device components for the load sensor 26, displacement sensor 24, and ETA 22. To simplify the fabrication process, the central stage 34c of the ETA and the movable shuttle 34a of the displacement sensor remained connected. This simplification removes a number of post processing steps required to join two separate shuttles. Wafers are diced into sensor chips. The sacrificial oxide layer, Oxide 1 and 2, are etched away and the chips are transferred into a developer prior to drying to complete the release process. Once released, chips are wire bonded and packaged for testing.

Figure 8:
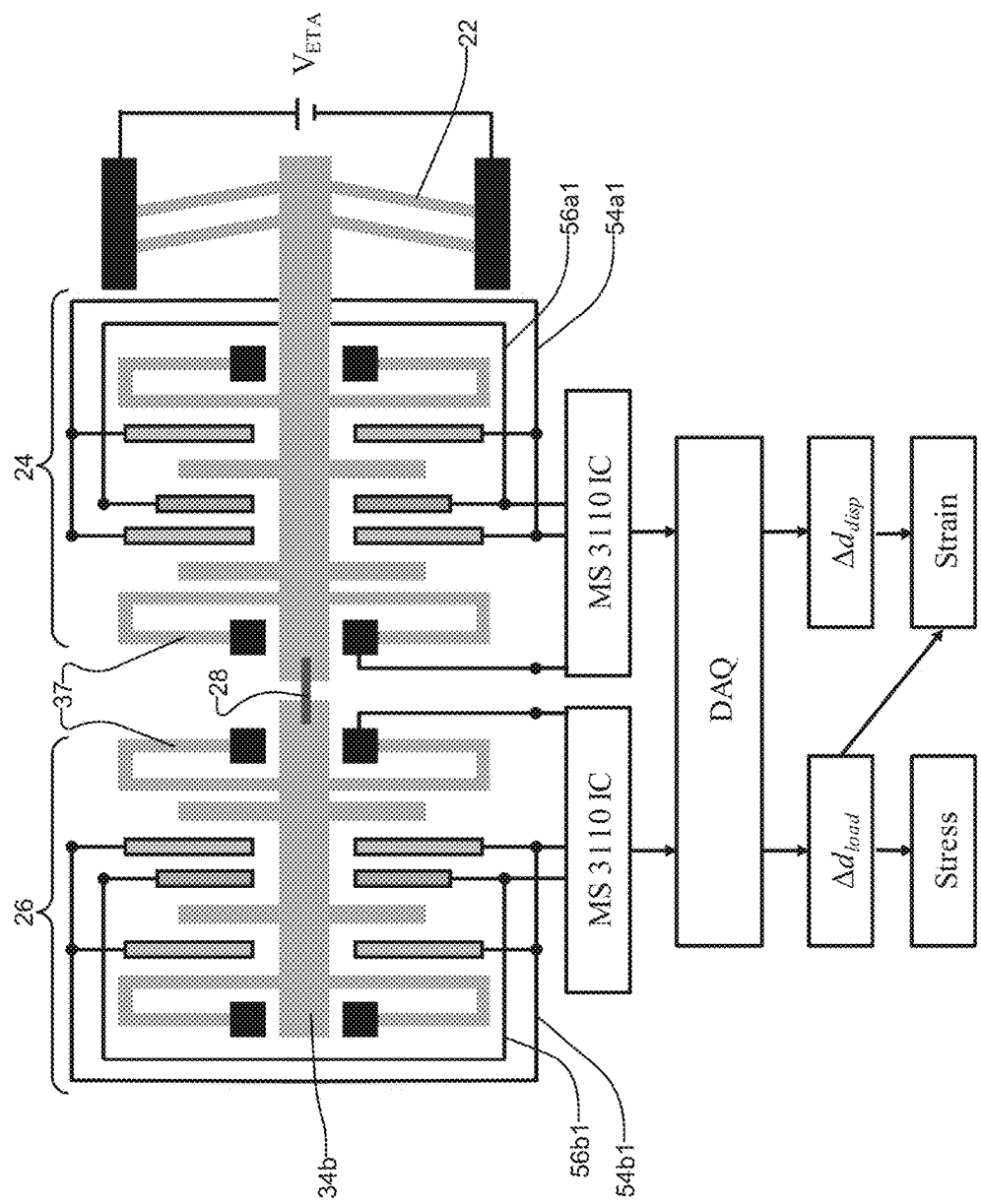
FIG. 8 is a schematic of the electrical circuits for the thermal actuator and the capacitive sensors.

The tensile testing method begins by connecting a tester 20 or 20a with an integrated AM specimen 28 to the power and measurement electronics as shown in the FIG. 8 schematic. A DC voltage supply generates the current for heating the ETA 22, which pulls on the specimen 28. The displacement sensor 24 and load sensor 26 are connected to capacitive readout sensors (MS3110 IC) which uses an AC signal to convert differential capacitances arising from the change in shuttle 34a and 34b positions into output voltages. A data acquisition system reads the output voltages and calculates the shuttle displacement for the displacement sensor 24 and load sensor 26. Those displacements combined with the load sensor 26 stiffness generate the engineering stress and engineering strain tensile curve for that AM specimen 28. In generating the stress-strain curve for the AM specimen, the instantaneous displacement of the specimen material is measured as the difference between the displacements of the two movable shuttles and the instantaneous force experienced by the specimen material is evaluated from the product of the axial stiffness ($K_{LS}$) of the second movable shuttle 34b and the displacement ($X_{LS}$) of the second movable shuttle. In lieu of capacitive sensors, a digital image correlation (DIC) technique may be used to measure the displacements of the ends of the specimen 28 during stretching or stretch release. The DIC technique may be used to calibrate the capacitive sensors.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A microelectromechanical device for mechanical characterization of a specimen, the device comprising:
   a substrate;
   at least one first flexure bearing supported on the substrate;
   a first movable shuttle having first and second ends, and being supported above the substrate by the at least one first flexure bearing so as to be free to move linearly relative to the substrate;
   a second movable shuttle having first and second ends, and being supported on the substrate through at least one second flexure bearing so as to be free to move linearly relative to the substrate, wherein the first ends of the first and second movable shuttles are positioned adjacent one another but are separated by a gap, and wherein the first and second movable shuttles are formed from an electrically conductive material;
a thermal actuator connected to the first end of the first movable shuttle, wherein the entirety of the first movable shuttle is a conductive, single layer, monolithic unit, and wherein the specimen is directly formed on or secured to the first ends of the first and second movable shuttles, such that the thermal actuator moves the first movable shuttle in a direction parallel to the surface of the substrate in response to a signal applied to the thermal actuator;
a first capacitive sensor formed between the first movable shuttle and the substrate; and
a second capacitive sensor formed between the second movable shuttle and the substrate.

2. The device of claim 1, further comprising:
a specimen object secured to the first ends of the first and second movable shuttles and bridging the gap between the first and the second movable shuttle; and
wherein the specimen object comprises at least one of:
an additively manufactured part,
a plurality of biological cells,
a soft material, and
a 2D nanosheet material.

3. The device of claim 1, further comprising a heat sink connected to the first movable shuttle to thermally isolate the first movable shuttle from the thermal actuator.

4. The device of claim 1, wherein:
the first and the second movable shuttles each have a bottom surface, and
the bottom surfaces each include a plurality of dimples.

5. The device of claim 1, wherein the first capacitive sensor includes:
first and second sets of parallel plates;
the first set of parallel plates being movable and attached to the first movable shuttle, and the second set of parallel plates being stationary and attached to the substrate.

6. The device of claim 1, wherein the second capacitive sensor includes:
first and second sets of parallel plates;
the first set of parallel plates being movable and attached to the second movable shuttle, and the second set of parallel plates being stationary and attached to the substrate.

7. The device of claim 1, wherein at least one of the first and second flexure bearings comprises a double parallelogram flexure bearing.

8. The device of claim 1, wherein the at least one first flexure bearing comprises a plurality of linearly spaced apart first flexure bearings, and each one of the linearly spaced apart first flexure bearings each comprise a double parallelogram flexure bearing.

9. The device of claim 1, further comprising:
a central stage; and
wherein the thermal actuator comprises a set of chevron beams that are connected to the central stage on a first end thereof and to the substrate on a second end thereof, and wherein the central stage is connected to the first movable shuttle of the device.

10. The device of claim 9, wherein the first movable shuttle, the connection between the first movable shuttle and the thermal actuator, and the central stage of the thermal actuator are made of the same material.

11. The device of claim 1, wherein a longitudinal axis of the first movable shuttle is collinear with a longitudinal axis of the second movable shuttle.

12. The device of claim 1, wherein the connection between the first movable shuttle and the thermal actuator comprises a rigid connection.

13. The device of claim 1, wherein the gap between the first and second movable shuttles is between 1 to 250 micrometers.

14. The device of claim 1, wherein:
the at least one first flexure comprises at least three distinct first flexure bearings spaced apart along the first movable shuttle for supporting the first movable shuttle at its first and second ends thereof and also at least at one midpoint along a length of the first movable shuttle; and
the at least one second flexure comprises at least three flexure bearings for supporting the second movable shuttle at the first and second ends thereof and also at least at one midpoint along a length of the second movable shuttle.

15. The device of claim 1, further comprising electrical contact pads to connect the thermal actuator and the two capacitive sensors to at least one external electronics circuit.

16. A method for mechanical characterization of a specimen material using a microelectromechanical system (MEMS) device, the method comprising:
applying specimen material across a gap formed between adjacently positioned ends of a conductive first movable shuttle and a conductive second movable shuttle, such that the specimen material is rigidly affixed to the ends of the first and second movable shuttles, and wherein an entirety of the first movable shuttle is a conductive, single layer, monolithic unit, and wherein the specimen is directly formed on or secured to the adjacently positioned ends of the first and second movable shuttles;
axially moving the first movable shuttle to stretch or compress the specimen material in controlled fashion; and
measuring a displacement of each one of the first and second movable shuttles.

17. The method of claim 16, further comprising:
evaluating the instantaneous displacement of the specimen material as the difference between the displacements of the two movable shuttles; and
evaluating the instantaneous force experienced by the specimen material from the product of the axial stiffness of the second movable shuttle and the displacement of the second movable shuttle.

18. The method of claim 16, further comprising the step of maintaining the first movable shuttle at a zero bias voltage during displacement recording.

19. The method of claim 18, wherein applying the specimen material further comprises an operation of development of the specimen material in one or more liquid mediums to wash away undesired sections of the specimen material.

20. The method of claim 19, wherein displacements of the first and second movable shuttles are measured by capacitive sensors.

21. Method of claim 19, wherein displacements are measured by digital image correlation.

22. A method for forming a device able to perform mechanical characterization of submicron features of a specimen material, the method comprising:
supporting a first conductive, movable shuttle above a substrate using a thermal actuator and at least one first flexure bearing;
supporting a second conductive, movable shuttle above the substrate using at least one second flexure bearing;

arranging opposing ends of the first and second movable shuttles adjacent one another to enable the specimen material to be applied to, and to bridge the opposing ends;

arranging a thermal actuator in contact with the first movable shuttle to cause linear movement of the first movable shuttle when a signal is applied to the thermal actuator, and thus to apply at least one of a tensile stress and a compressive stress to the specimen material, an entirety of each of the first and second movable shuttles forming separate, single layer monolithic units;

arranging a capacitive sensing subsystem adjacent the first and second movable shuttles, such that a displacement of both of the first and second movable shuttles is detectable for subsequent analysis; and wherein the specimen material is directly formed on or secured to the opposing ends to bridge a gap formed between the opposing ends of the first movable shuttle and the second movable shuttle, such that the specimen material is rigidly affixed to the opposing ends of the first and second movable shuttles.

* * * * *